(12) United States Patent
Gan et al.

(10) Patent No.: US 6,468,774 B1
(45) Date of Patent: Oct. 22, 2002

(54) ISOLATED HUMAN ENZYME PROTEINS, NUCLEIC ACID MOLECULES ENCODING HUMAN ENZYME PROTEINS, AND USES THEREOF

(75) Inventors: Weiniu Gan, Gaithersburg; Fangcheng Gong, Germantown; Valentina Di Francesco, Rockville; Ellen M. Beasley, Darnestown, all of MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/822,862

(22) Filed: Apr. 2, 2001

(51) Int. Cl.[7] .......................... C12N 9/08; C12N 15/00; C12N 5/00; C12N 1/20; C07H 21/04
(52) U.S. Cl. ................. 435/192; 435/320.1; 435/325; 435/252.3; 536/23.2
(58) Field of Search ................ 536/23.2; 435/320.1, 435/325, 252.3, 192

(56) References Cited

PUBLICATIONS

Product information for bovine erythrocyte glutathione peroxidase, Calzyme Laboratories, Inc., 1997.*
Product information for catalog No. 21014, Oxis Research, 1999.*

* cited by examiner

Primary Examiner—Rebecca E. Prouty
Assistant Examiner—David J. Steadman
(74) Attorney, Agent, or Firm—Applera Corporation; Lin Sun-Hoffman

(57) ABSTRACT

The present invention provides amino acid sequences of glutathione peroxidase polypeptides that are encoded by genes within the human genome. The present invention specifically provides isolated peptide and nucleic acid molecules, methods of identifying orthologs and paralogs of the enzyme peptides, and methods of identifying modulators of the enzyme peptides.

9 Claims, 8 Drawing Sheets

```
   1 GCCAGGGATC AGGCAGCGGC TCAGGCGACC CTGAGTGTGC CCCCACCCCG
  51 CCATGGCCCG GCTGCTGCAG GCGTCCTGCC TGCTTTCCCT GCTCCTGGCC
 101 GGCTTCGTCT CGCAGAGCCG GGGACAAGAG AAGTCGAAGG CTCCCCGCCA
 151 GATGGGCAAT CCCCAGATGG ACTGCCATGG TGGCATAAGT GGCACCATTT
 201 ACGAGTACGG AGCCCTCACC ATTGATGGGG AGGAGTACAT CCCCTTCAAG
 251 CAGTATGCTG GCAAATACGT CCTCTTTGTC AACGTGGCCA GCTACTGAGG
 301 CCTGACGGGC CAGTACATTG AACTGAATGC ACTACAGGAA GAGCTTGCAC
 351 CATTCGGTCT GGTCATTCTG GGCTTTCCCT GCAACCAATT TGGAAAACAG
 401 GAACCAGGAG AGAACTCAGA GATCCTTCCT ACCCTCAAGT ATGTCCGACC
 451 AGGTGGAGGC TTTGTCCCTA ATTTCCAGCT CTTTGAGAAA GGGGATGTCA
 501 ATGGAGAGAA AGAGCAGAAA TTCTACACTT TCCTAAAGAA CTCCTGTCCT
 551 CCCACCTCGG AGCTCCTGGG TACATCTGAC CGCCTCTTCT GGGAACCCAT
 601 GAAGGTTCAC GACATCCGCT GGAACTTTGA GAAGTTCCTG GTGGGGCCAG
 651 ATGGTATACC CATCATGCGC TGGCACCACC GGACCACGGT CAGCAACGTC
 701 AAGATGGACA TCCTGTCCTA CATGAGGCGG CAGGCAGCCC TGGGGGTCAA
 751 GAGGAAGTAA CTGAAGGCCG TCTCATCCCA TGTCCACCAT GTAGGGGAGG
 801 GACTTTGTTC AGGAAGAAAT CCGTGTCTCC AACCACACTA TCTACCCATC
 851 ACAGACCCCT TTCCTATCAC TCAAGGCCCC AGCCTGGCAC AAATGGATGC
 901 ATACAGTTCT GTGTACTGCC AGGCATGTGG GTGTGGGTGC ATGTGGGTGT
 951 TTACACACAT GCCTACAGGT ATGCGTGATT GTGTGTGTGT GCATGGGTGT
1001 ACAGCCACGT GTCTACCTAT GTGTCTTTCT GGGAATGTGT ACCATCTGTG
1051 TGCCTGCAGC TGTGTAGTGC TGGACAGTGA CAACCCTTTC TCTCCAGTTC
1101 TCCACTCCAA TGATAATAGT TCACTTACAC CTAAACCCAA AGGAAAAACC
1151 AGCTCTAGGT CCAATTGTTC TGCTCTAACT GATACCTCAA CCTTGGGGCC
1201 AGCATCTCCC ACTGCCTCCA AATATTAGTA ACTATGACTG ACGTCCCCAG
1251 AAGTTTCTGG GTCTACCACA CTCCCCAACC CCCCACTTCT ACTTCCTGAA
1301 GGGCCCTCCC AAGGCTACAT CCCCACCCCA CAGTTCTCCC TGAGAGAGAT
1351 CAACCTCCCT GAGATCAACC AAGGCAGATG TGACAGCAAG GGCCACGGAC
1401 CCCATGGCAG GGGTGGCGTC TTCATGAGGG AGGGGCCCAA AGCCCTTGTG
1451 GGCGGACCTC CCCTGAGCCT GTCTGAGGGG CCAGCCCTTA GTGCATTCAG
1501 GCTAAGGCCC CTGGGCAGGG ATGCCACCCC TGCTCCTTCG GAGGACGTGC
1551 CCTCACCCCT CACTGGTCCA CTGGCTTGAG ACTCACCCCG TCTGCCCAGT
1601 AAAAGCCTTT CTGCAGCAAA AAAAAAAAAA AAAAAAAAAA AAAAAAAAAA
1651 AAAAAAAAAA AAAAAA
     (SEQ ID NO: 1)
```

FEATURES:
5'UTR:        1 -52
Start Codon:  53
Stop Codon:   758
3'UTR:        761

Homologous proteins:
Top 10 BLAST Hits

```
                                                               Score       E
Sequences producing significant alignments:                    (bits)   Value
CRA|18000005086067 /altid=gi|2160390 /def=dbj|BAA00525.1| (D006...  460   e-128
CRA|18000004948833 /altid=gi|121672 /def=sp|P22352|GSHP_HUMAN P...  460   e-128
CRA|1000682331403 /altid=gi|6006001 /def=ref|NP_002075.2| plasm...  453   e-126
CRA|18000004952103 /altid=gi|121673 /def=sp|P23764|GSHP_RAT PLA...  425   e-118
CRA|18000004932639 /altid=gi|6680077 /def=ref|NP_032187.1| glut...  420   e-116
CRA|18000004971804 /altid=gi|1170039 /def=sp|P46412|GSHP_MOUSE ...  420   e-116
CRA|164000136745254 /altid=gi|11968108 /def=ref|NP_071970.1| pl...  418   e-115
CRA|18000004952102 /altid=gi|585223 /def=sp|P37141|GSHP_BOVIN P...  414   e-114
CRA|18000004882520 /altid=gi|163706 /def=gb|AAA16579.1| (L10325...  414   e-114
CRA|18000005050736 /altid=gi|2117626 /def=pir||JC4550 glutathio...  409   e-113
```

FIGURE 1, page 1 of 2

EST
>gb|BF339668|BF339668 602038948F1 NCI_CGAP_Brn64 Homo sapiens cDNA clone IMAGE:4186979
5', mRNA sequence.    1120    0.0
>gb|BE743665|BE743665 601574121F1 NIH_MGC_9 Homo sapiens cDNA clone IMAGE:3835108 5',
mRNA sequence.    1098    0.0
>gb|BE910406|BE910406 601503388F1 NIH_MGC_70 Homo sapiens cDNA clone IMAGE:3905156 5',
mRNA sequence.    1041    0.0
>gb|BF127569|BF127569 601810219F1 NIH_MGC_46 Homo sapiens cDNA clone IMAGE:4053125 5',
mRNA sequence.    961    0.0
>gb|BF182929|BF182929 601809867F1 NIH_MGC_18 Homo sapiens cDNA clone IMAGE:4040465 5',
mRNA sequence.    952    0.0
>gb|AI878994|AI878994 au53b08.y1 Schneider fetal brain 00004 Homo sapiens cDNA clone
IMAGE:2518455 5' similar to gb:X58295_rna1 PLASMA GLUTATHIONE PEROXIDASE PRECURSOR
(HUMAN);, mRNA sequence.    886    0.0

EXPRESSION INFORMATION FOR MODULATORY USE:
>gb|BF339668|BF339668  Brain glioblastoma cell line
>gb|BE743665|BE743665  Ovary adenocarcinoma cell line
>gb|BE910406|BE910406  Panceras epitheloid carcinoma
>gb|BF127569|BF127569  Uterus leiomyosarcoma
>gb|BF182929|BF182929  Lung large cell carcinoma
>gb|AI878994|AI878994  Fetal brain Tissue expression:
Human whole_liver FIGURE 1, page 2 of 2

```
  1 MARLLQASCL LSLLLAGFVS QSRGQEKSKA PRQMGNPQMD CHGGISGTIY
 51 EYGALTIDGE EYIPFKQYAG KYVLFVNVAS YCGLTGQYIE LNALQEELAP
101 FGLVILGFPC NQFGKQEPGE NSEILPTLKY VRPGGGFVPN FQLFEKGDVN
151 GEKEQKFYTF LKNSCPPTSE LLGTSDRLFW EPMKVHDIRW NFEKFLVGPD
201 GIPIMRWHHR TTVSNVKMDI LSYMRRQAAL GVKRK
    (SEQ ID NO: 2)
```

FEATURES:
Functional domains and key regions:
[1] PDOC00005 PS00005 PKC_PHOSPHO_SITE
Protein kinase C phosphorylation site Number of matches: 2
    1    127-129 TLK
    2    175-177 SDR

------------------------------------------------------

[2] PDOC00006 PS00006 CK2_PHOSPHO_SITE
Casein kinase II phosphorylation site 48-51 TIYE

------------------------------------------------------

[3] PDOC00008 PS00008 MYRISTYL
N-myristoylation site

Number of matches: 3
    1    24-29 GQEKSK
    2    43-48 GGISGT
    3    44-49 GISGTI

------------------------------------------------------

[4] PDOC00396 PS00460 GLUTATHIONE_PEROXID_1
Glutathione peroxidases active site 70-85 GKYVLFVNVASYCGLT

------------------------------------------------------

[5] PDOC00396 PS00763 GLUTATHIONE_PEROXID_2
Glutathione peroxidases signature 2

106-113 LGFPCNQF

Membrane spanning structure and domains:

| Helix | Begin | End | Score | Certainty |
|---|---|---|---|---|
| 1 | 3 | 23 | 1.316 | Certain |
| 2 | 69 | 89 | 0.837 | Putative |
| 3 | 95 | 115 | 0.748 | Putative |

FIGURE 2, page 1 of 2

BLAST Alignment to Top Hit:
```
>CRA|18000005086067 /altid=gi|2160390 /def=dbj|BAA00525.1| (D00632)
         glutathione peroxidase [Homo sapiens] /org=Homo sapiens
         /taxon=9606 /dataset=nraa /length=226
         Length = 226

Score =  460 bits (1172), Expect = e-128
 Identities = 225/235 (95%), Positives = 225/235 (95%)
 Frame = +2

Query: 53   MARLLQASCLLSLLLAGFVSQSRGQEKSKAPRQMGNPQMDCHGGISGTIYEYGALTIDGE 232
            MARLLQASCLLSLLLAGFVSQSRGQEKSK         MDCHGGISGTIYEYGALTIDGE
Sbjct: 1    MARLLQASCLLSLLLAGFVSQSRGQEKSK---------MDCHGGISGTIYEYGALTIDGE 51

Query: 233  EYIPFKQYAGKYVLFVNVASY*GLTGQYIELNALQEELAPFGLVILGFPCNQFGKQEPGE 412
            EYIPFKQYAGKYVLFVNVASY GLTGQYIELNALQEELAPFGLVILGFPCNQFGKQEPGE
Sbjct: 52   EYIPFKQYAGKYVLFVNVASYXGLTGQYIELNALQEELAPFGLVILGFPCNQFGKQEPGE 111

Query: 413  NSEILPTLKYVRPGGGFVPNFQLFEKGDVNGEKEQKFYTFLKNSCPPTSELLGTSDRLFW 592
            NSEILPTLKYVRPGGGFVPNFQLFEKGDVNGEKEQKFYTFLKNSCPPTSELLGTSDRLFW
Sbjct: 112  NSEILPTLKYVRPGGGFVPNFQLFEKGDVNGEKEQKFYTFLKNSCPPTSELLGTSDRLFW 171

Query: 593  EPMKVHDIRWNFEKFLVGPDGIPIMRWHHRTTVSNVKMDILSYMRRQAALGVKRK 757
            EPMKVHDIRWNFEKFLVGPDGIPIMRWHHRTTVSNVKMDILSYMRRQAALGVKRK
Sbjct: 172  EPMKVHDIRWNFEKFLVGPDGIPIMRWHHRTTVSNVKMDILSYMRRQAALGVKRK 226 (SEQ ID NO: 4)

Hmmer search results (Pfam):
Scores for sequence family classification (score includes all domains):
Model    Description                                        Score    E-value  N
-------- -----------                                        -----    -------  ---
PF00255  Glutathione peroxidases                            255.6    6.6e-73  1

Parsed for domains:
Model    Domain  seq-f  seq-t     hmm-f  hmm-t    score    E-value
-------- ------- -----  -----     -----  -----    -----    -------
PF00255  1/1     48     162 ..    1      119  []   255.6    6.6e-73
```

FIGURE 2, page 2 of 2

```
   1 AACACCTTTG AGAGCAGGGA CTTTGGCTTT TAGACAACTC TTTAGCATCT
  51 CTCATGGTGT TAACATGTTG CTAGGTGCCT ATTTTGAGGG TCACTAGATG
 101 CCTACTGATA CTAATGAACA ATGGATTTCT GACAAACTGA TGTGCACACA
 151 GATGTTTATA TTTTAGGGTA AATACGAACC TTAAAAGACA ACAGAACAAC
 201 ATGGAGAGGG CCTGAGACTG AGTCTAGAGA CCTGGATTCT GGTTCCCTCC
 251 CTGCCATCAG TTGGTTATGG GAACTTGGAT AAATTGCTCC TCATCTCTAG
 301 GCTTCAGGGA AATGAGGTGG TTGAATAAAA CGTATTGAGC ACTTACTGTG
 351 TGTCAGCCAT TGTTCATATG CTCCCAGGCT TTAACTCAGC TAAAGACTTC
 401 CCTGGCCTCT GTGGTTCCTT CCACTTCAAC AGGCTGTGGT TTGAGGTGGG
 451 AAGCTTCGT AGAGAATGCA AAACTTGAGA GACATCTTCC AAATTCCCAG
 501 GGGGATGTTA ATACCTTTAA TCATAGTAAA GGTATGGTTT CTCAAGGCAT
 551 TTCTTGGTCA GAAGAAAGTT CCAGAAGGCA CTTAATCCTA GGACTCACAC
 601 TACCAAGGCT ACAGCCAGGC CAACTGCCTC ACAATAACCT TAGAACATGT
 651 CTGAAGACAG ATTTTCAGCT TCTGCCCCTA GACATTCTAA TGCAGTGATT
 701 CCAAAGTGGG GTCCAGGAAT CTGTATTAAA GGCTTCCCAG TTGACTCTGG
 751 TGGTCAGAGA GATTTGAGAC TGATTCCATC ACATTCCCCA TCTGTGAACG
 801 GGATCATACC TAGACAGCCC AGCCCTAGAA CTGCCTGGTC TGATCCTAAG
 851 TGTTCCATGG AGATTTTGTT TTTTTAATGT AATGAATGAT TAAGTCAGCA
 901 AATACTTTAC ATCTCTTGTG TGCTAGGCCC TGTGCCAGGT GGTGATTATG
 951 GGCCCTATTC TCAAAGGACT CCTGGTCTCC GTCTGTCACT TACTTTAGAA
1001 ACAAGTCATC TAGCCAGAGC CAGAAGGGCA CTGGAGATCA CTAATCAATC
1051 CCATCATTAC ATAGCTGAGG AAACTGAGGC CAGAGAGTA ACTGCAACAT
1101 GTTAAAGACT ACACAGGGAG CAAATTTATT TTCTGCTTCT AAGCCAGGTG
1151 GTTTGGCCAC AGATAGGCCA AGAAGAATAC GAACAGACAA GCCTTGCTGG
1201 GTTTCCCACT CAGTTTATTA CTATTAGACC ATTCCCTTTT TCCCCACTCA
1251 CATTTCTGCG CATTTCCATG GTCTTCATAG AATCTAAGCC TAAAAATAGA
1301 GTTTTCCTTG AGTCTTTGGG TCTTCATTTC TGAAGACTCT CATGTCACAG
1351 AAAACTTTAA TTAAATAAAT CGTTATGCTT TTCTCTTGCT AACCTTTTTC
1401 TACAGGCATG TCAGCTGTGA TCCTTATGAT GGGGAGGAAA GGCACCCCAC
1451 CTTCTCTGTC CCTACAGTCC TAATGCCCTA CCCAGAATGG GGTTTTCAAA
1501 ATCCCAGGAC ACCCACTCTT TGTTTCTTAA GCACTAAACC TATATATAGT
1551 AAATGTTTCT GGAAGTTTAA CTTCAGCTCT TGCTGAAATT TTAAACCCTC
1601 AATTTCCAGA GGACCATCGC CAGGTGTTTT TAAAACCTCG ATAGGAATAA
1651 GAAATGCTTC CCAGAATGGA GACTTCCATC AGTTCTAGGG AGCTATTAGC
1701 CCCCTTGCCC TGGCTGTAAT GGAGACCGCT GTGTCTGCCT CCTTTCGCAC
1751 TTTGGAGCCA AAAGAGGAAG GGACCGCCTC CCACGTCCAC AGGGACCTGA
1801 CTTCCACCTC TCTGCCCAGA TTTGCTTATG TCACTGTCGC CCCGGGACGG
1851 GGAGGTGGGG AGCTGAGGGC AAGTCGCGCC CGCCCCTGAA ATCCCAGCCG
1901 CCTAGCGATT GGCTGCAAGG GTCTCGGCTT GGCCGCGGAT TGGTCACACC
1951 CGAGGGCTTG AAAGGTGGCT GGGAGCGCCG GACACCTCAG ACGGACGGTG
2001 GCCAGGGATC AGGCAGCGGC TCAGGCGACC CTGAGTGTGC CCCCACCCCG
2051 CCATGGCCCG GCTGCTGCAG GCGTCCTGCC TGCTTTCCCT GCTCCTGGCC
2101 GGCTTCGTCT CGCAGAGCCG GGGACAAGAG AAGTCGAAGG TGAGTGAGCC
2151 TCCGGGCCGG GGGCCGGGAG AAAAAACCTA GCCCCTCGGT GTCCAGCGCT
2201 CAGTGCAATG CACCCCTTTT CCCAGGCTCC CCGCCAGATG GGCAATCCCC
2251 AGGTGCGAGA GACCTCCTGA ACCCCTTTTG CCGCCCCCTC CGCCGCCGGG
2301 ACCCCGCCCC CGACCGTCGT CGTCTCGTAG TTCCATCTGT TGGAGAGCCG
2351 AGACCTGGTG CTTCAGGCGG GCAGAATGAC TAAGGGAGGA AGGTCTCTCT
2401 CCCCGAGCTC GCACTTTCTC CCCACTGCCA CCTCGAGGGT CGCCTTGCTA
2451 CATCTATGTC ACCTCCGTGC CTGAGCTGCT CCCCTTCAGT AGGGCCTAAG
2501 AGGGAGGGCG TCACAGAAAA AAATGCCCAG CGTCTGGGTG GGCTGTGCAA
2551 GTTCCCAGGG AGAGAGACAA GGAGAAAGGA GAGAGGCAGC TGGGTGGTCC
2601 TGGTCCTGAA GAACTGCTGT GGGGGGCTCT TCTACCCCAA GAATGATACA
2651 GGCAGGTAGA AATGGCCACT TGGATTCAGG GCATTGGTAG AAGAGGCAGA
2701 GATCTGTGCT AGAAAGAGCT CTGGAGTGAC AGTGCAGAAC ACTCAGGACC
2751 CTGAGTCCTT ACCTGCTCCT GGACCCCGT TTCTCCATCT GCAGGGGAGA
2801 GTTTGGGGGT GGGAGTGCAT GGGGCACAAT GAAGCTGAGG GCCTCAGAGG
2851 GGATGCTTGG AGAAGCTGAA AAATCCACAA GCTGTTCTCT GAAATTTCCT
2901 CCCCTGGGC AGCCTCACTA CCCAGGACCC ACTGTCCTCA TTAGCCTGAG
2951 GAAACCTGGT AGTTGGAGAA AGCTGGGAC TGCTAATTCA GAAGAAGAGG
3001 TAGAATTCTC TAGAGCCTCA GTCTATTTCC AGCAGGTGTG TGGCCCACAC
3051 CTGGAGTGGG GATACTGAGG CCAGGAGTGG GATGACCCAG CATGCTTATC
3101 TCCTTTGACA GTATGTACTG GGGTGGGCTC TGTAGACCTC TCCTCTACCC
3151 AGGGAGTGGG AGTGGGTGGG GAAGGAGGCA GAAGCCAGGT GTAGGGATAG
3201 ACTCAAAGCG AGCGATTTCT GTCTCCAACT TCCCAACATG CATAACTCAC
3251 ATTTTTGCAA GCTCTGAGCT TTTGTTTCTA AAATCCTCTG GGTCTTCACT
3301 TTAATTAAGT TCTTATGAGT CTAGGATTCC GTTTCCAAAA TTCTGTCCAC
3351 TTCTCAGGAA GCCCATTGGA AGCACAGGGT TCCTTCCATG TTACTCACCC
3401 CTTTTCGGTC CTCAGCCTAA ATCCGATTAA TCAGCCTCTC CTTGGAGTCA
3451 GTCTAAATGG ATGTGAAGCC ACTTCGTCCA AGTCCCCTCC TTTTTATCCA
3501 TCCCTGTTCA TAATCCCCAA CTCAGAAGGC ATTTTCCAGG TCAGGAATGG
```

FIGURE 3, page 1 of 4

```
3551  GATCGATTTT CAACATTGAG GTTTGGGGTG GGCCATAGAC AGGCCAGCAC
3601  CGTGGAGTCA GTCCCAACCT TCAGTTTTGG AAGGGTCAAA GAAGATACAA
3651  TTGGGCCCTG CCTCAAGAAG GCTAGTGGGG AGAACGTGGA CTCCATGAAT
3701  AACTCATCAT AGCTGTGTCT TCTCTGCCGC ACTCTGGGGA AGGATAAATG
3751  GACTCAGAGA GAATAGGATG GGGATGGTCT AGAAAAGTTT TAGGGTGAGG
3801  TGTGATCATA TCACATACAA CCAGTCAGGA CTTGCTGGCT AATGAAAGCC
3851  TGGGCATGCC CATCTCTGCT CCCAAGTTCT TAGAGTTCAG ATGTCTTAGC
3901  TCTGGGTTAG GACCCAACCA CTCACCTTAC CCCCAACCCC AGGGTAAAGA
3951  GATAGGGTTA TGGGGCATGT GGAGAATGGA ATGGACGAAA GGTGACTCAG
4001  CCCCAGAGAG GTGTTTTCCT CCTACCAATT GAAAGGGAGA TGCTAGGGAA
4051  GAGACCAGGT CCTCCTCTTC TTGCTGCGTC ACCTCCCCAG TCCAACTTCA
4101  GGCTGCCCAC GCTCCTTGTC TCTACAAAAG GACTGCAGAA GCCGGAAAGA
4151  GTGACAACTG CTGACGTGCA TGGGATCCTA GTAACTGCTG GTTTCTAGGT
4201  GACTAAACCT GGCAGAGAGA ATCATGGAAC CACAGGCTGA CAGAGTTAAA
4251  GGGCCCTTAA GACAGCCCTG AACCTGACTC CATCTTACAA TGGAGGAGCT
4301  GGAGCCCCAG CAAAGGGGGT CACATGCCAT CAGAGACACA GCAAAGCCCA
4351  GCACTCAGGT CTCCTGACTC CCAGACCACT TCTCACAGCA TCATATTGAT
4401  AGGAGTGATA AGACGGGAGA GGAGAAAGAC ACAAGACCAG CAGCCCCAGC
4451  CAGCCAGAGT CCTGGCTGAG TCCCATCATC CAACTCTCAA GCCATTGGAA
4501  CCCTCTTCTC TTGCCCGGCT GTGGGAGGAT TCAGGCACCC TCATGCCCTC
4551  TCCCCTTATC TCCTCTGGCC ACTGTTTCAG ATGCGGTGCT CTGGGATTCC
4601  ACGTGCCCAG AGAAGGGAAG GGGGCTCATA GAGGACTGAG TTGCAGTGAT
4651  CAGTGGTGAG CACAGCCGTG GCTCTCCACC CATGGGCCAC CTTCTGACCC
4701  CCACTATCCC TTGACATGAG ATTTCGTTCC AAGAGACTCC AGGCCTGTTT
4751  TGCTCTGCCA GCAGATTCCC ACAACCGTTT TGGGCAGCAG CATGCTTATC
4801  TCCCTGGACA TATGCCCAGA CAGTGTAAGT GACTTGCTCA GGGCCACGCA
4851  GCCAGCAAAA AATAGAACCT AATGAAATAG GGTTCTCCTT GCCACACCCC
4901  CAAGCTGAAA CTGTGCCCAG AAGCTGGTCC TTCTGTTTAC AAGTTCCCAT
4951  TATTAGGACA ACCTGTAATC TTTTTTTCCT CCATGTCTCA GAGTTCATTT
5001  TTGGATCATG GCAGAGTTAA AAAAGTGGAG AGGCTATAGA CATGCCTGGC
5051  TTTCTGGCCA CTAGATCTTT GTGGCGGTCT AGGGTGTATT TGTTGTGCCC
5101  CAGTTTGTCT GCATTTTAAG GCGGAACTGG CCCTGGCTGG GAACGAGGAG
5151  GTCCAGGAGC AGTAGGAATG TTGATCTTAG GTCTTGGGCC TGCCTCCAGC
5201  ACCCACCAAA AGTCACCGGA TGTGGAATAT TAGACTCATG TAAAGCAGGA
5251  AGTTTGCACC AGAGCCAAGA AGAGAGCTTG CAGCTGCCAG GGAATGGCCT
5301  GGCGGAGGAA GCGCAGCCTC GCCCAGCTCA GCAGACCTGC TTCATGACAG
5351  AGGCAGCTCT TCTGCACTCT ACTGGGGCCA CGCCCTGCCA GCATATATCA
5401  CTCCCTTCAC CTGGTCAGGC CCAGGTACCT TGCCTCAACA GCAAGTTCTC
5451  CAGAATTGAG GGGAAGAGAG GGAGTGAATT TGCTTCTCTA ACTCCAGCCA
5501  CCTGTCTCTG CCCTCTCCTG GTCTATAATG CTACTTTGCA TTCCATTTGT
5551  TTATTGTCTG CCCACCTCTC AAAGGATATC AGGGCCACAA AGGACCTTAA
5601  AGACCACCTT ATACAATGGT TTCAAGGTTT CTCCTTTCCC ATCACGACCA
5651  GCCCACCTGC CAAATTGTGT CAATGATGCA ATGACATCCT TTCAAGAATA
5701  GTCTCAGAAT TTTGTTGTCT GTGTCACGGG CAGAGTAGGC TCATAGGCCA
5751  CATCCTACTA GCCAGCAGTG ACCCCAATCC CCTCTCTCCC ACTGATCATG
5801  ATCCTATCAA GCCATCATGG TTGACCTGGT TGAAGAGTTG GTTCAGTTCA
5851  AGGTTCTCAT TTTATAAATG AGGAAACTCA GGTCCGAAGA AAAGAAAGGG
5901  CCAGTCCAAG ACCACACAGG GAGTTAATGG CAGAGGGACA TGGAGCCCAG
5951  GTCTCCCAGC CCACAGTCCA CTGCACTCTG TCCCTCCTTG TCCTGGAGGC
6001  TGACTGTGAG CAGCAGCTGG GGAGGGAGGA AGGCATAAGG GTCATCACCA
6051  GCCTGCTCAG ACCCGGAACA TTAACACATG CAGGTACTGT TGCTTTTCCC
6101  TACCTCACCA CAGCCCTTTC CCCCATGCCT GGCTCTCAGT CCTGCTTCCC
6151  TATTTGGTAA CAACAGCTTC ATCTTTCCTG TCCTGCAGAT TGGGAGCCTC
6201  TGAATCACCA TGTCCATACT GCCTCTTCCT CCTTTCTGTT CAGTTTTTCC
6251  TTCACACTGG CCTAGTTCAG GTTCTCATCC TCAATTGCCT GGATTATTCC
6301  AACAGCCACC CAACCAGTCT CCATCAGCCC GTCTAGGAAC CCAGTCATCA
6351  GCTTTAGGGC AGTCTCCCTG AGAGCCCAGT AAATGTTCTG AAATTGACAT
6401  GTGATGTGGA AGTAATTAGC AAAATAAGTC ATTCTCCAGG GTTCCATAGC
6451  ACTCACTTAT TAAGTGCTTA ATATTAATAA GTGCTTATTA GGTGCTTAAT
6501  ATTAATAAGT GCTTTTTAAG CACTTAATAT TAAGTACCCG AAAAGCACTT
6551  ATTAAGTGCT TTCATAATCA TTATCTTAAA CAAGGAATTA GGAGACGTCA
6601  GTGCTAGTCC AGTTCCAATT CTCGGTGATT ACTTTGAGAA AGTCACTCTC
6651  TCTGTTGGGA TCTTTCATTC TTTTGAAAAC GGAGATGTCC AAGTTCCTTT
6701  CCAGCTCTAA CTGCTCCTTT TATGGCCTGT GTTCCAGATG GACTGCCATG
6751  GTGGCATAAG TGGCACCATT TACGAGTACG GAGCCCTCAC CATTGATGGG
6801  GAGGAGTACA TCCCCTTCAA GCAGTATGCT GGCAAATACG TCCTCTTTGT
6851  CAACGTGGCC AGCTACTGAG GCCTGACGGG CCAGTACATT GGTAAGAGCC
6901  CACCCTTCCT CCCTGCTTTA TTTGGGGCTG TATGGCATAT TTCAATCACA
6951  GGAGCTTTTC TGGTGCATGG GGGAAAGGGT GATGGCAATC ACGAGAGTCC
7001  AAGCCCCTTT TCTCAGCTCC ACTGTGTTCC GTGGTTTTGT GAAGATGATT
7051  ATATAAGCCT GAGGTCTGAT TGCCTTTGGA CATGTTCTAG GAGATTCCTA
```

```
 7101  GTTATCCTTC TTCATCTCTG GGCACCTCAA CAACCCTAAA GGCAGAGGGA
 7151  TAGAGATTAG GTTTGTGCTT AGAGCTCCCT TTGGCTGGAG CATGAGATGG
 7201  TAACTGAAGC TCCATCTTGC TGAGAATATC TCATTTTCCC TCAGCCCCAT
 7251  CTGCTTTGGT GCTTCTCTTG GCAGCTCTCT GGAAAGCAGG CAATTGCCTC
 7301  GAGGCCCCAG AGTGTATGCG TGGTGTAGCG GGATCAAGGA GCAGGCTACA
 7351  CTTCTAATGC CCATTCTAAA ATAAACTTTG AAGATGATCT AGTTTAGCCT
 7401  TCCCCTCTTC TCAATCTACA CATGGGAAAC CAAGACTCAG AGCGAAGATA
 7451  CAACTTAAAC AGGGTCACAA AGCTATTAGC GGTGGAATGG GGCATTTGGC
 7501  GCAGGTTTCA TGATCTCCTG ATATGCTTAC TCCTTTCTCC CTAGCTGGGG
 7551  TAGAATACAG AGGCTAGGGG AACAGGCAAC CAAAGGCAAG CGACAGCACC
 7601  CAGGGGAAAA CGCTTTGGGG CTGAGCAGTC TACTGGCAGG GGGTCAGGGA
 7651  GGCAAGGGCA ATTTGACCCT CCATGCTCTG CCTGGCAATC ACAGGCGAAT
 7701  TCCCGAAGT GAAAGGACGC CGGTCACGTG GCCCAGTGGC TGTGAGTGCT
 7751  TTTTCTGGGA TGCTTCTCTC TAGCCTTGGA ACAGAGCAGA GTGCGTTTGG
 7801  GCAAGAGATG GGCTGGGTGC TGCTGCAAAA GAGACCAGGG GACACTGAGG
 7851  AAACTGGGGA GCTGGGCCAG GGCCTCATCT GTGTTCCTGA TTTGCCAAAG
 7901  ATTATGGGAG GGTTGTAACC TCACCCCAAA GAAGTTCTCT GCCTTGTATC
 7951  CAGGGATGGA TAGTTCTTGC TCCAGAAAAC TCAATCCTGA GGGTTCTGAA
 8001  TGAGTGCTCT AGCTGGCCCA GGTGGAGGGC CTTGGCAATG GGCAGGTGAC
 8051  TGACAGCTGA CTTGAGGAAG GGTATTATTC TTGTCCTCCA AACCTCCAAT
 8101  CCATCCAGAT TAGAGTCAAG AGGATAGGAC CTGAGTCCCA GCATTGCTGT
 8151  GAACTCACTG GTGATCCTGC GCAAGTCCCT CCCTTTCTCG GGCCTCAGTA
 8201  GTTCCAGCGG CACAGCGGGT GAGCCGGGGG AGTGGTGTGG ATGAGACAGG
 8251  GCTCCTCGCC AGGATACTCC CACATCTGCT CTTTCTCTTT GGCCCAGAAC
 8301  TGAATGCACT ACAGGAAGAG CTTGCACCAT TCGGTCTGGT CATTCTGGGC
 8351  TTTCCCTGCA ACCAATTTGG AAAACAGGAA CCAGGAGAGA ACTCAGAGAT
 8401  CCTTCCTACC CTCAAGTGAG TACTCACTCA GCATCCTGAG AAAGCTCCTC
 8451  TCACATGGCC CACATCTTGT TATCAACCCC AAATCATGGT GGACATTTAT
 8501  CGGCCACCAA GAACTACTCT CCTCTTCTAG GATCCCCAGT GGAATGAGGG
 8551  AAGGGAAGGG ACAAGAGAGG GAGAAGGACA GGGACAACTG GTTGTGATGT
 8601  GCATCCGCAG GGAGCACCAA GGTTGAGGGA CACTGAAAAG GGACCAGGCT
 8651  AGAAAGGAAG ACCGTGGACT CACATTATGC CTATGCCCAC TGCACATTCA
 8701  CTGGCTCCTG CTGCCCACTG CAGAATAAAT CCAGACTCCC AACACCCTCT
 8751  CCCCTGTTCT GTCCCTTCCT CTCATTTCTG AGCCCTGTGC CCACCTCCTT
 8801  GGGACCCACC TAAGAACATT TCTCAACAGG TATGTCCGAC CAGGTGGAGG
 8851  CTTTGTCCCT AATTTCCAGC TCTTTGAGAA AGGGGATGTC AATGGAGAGA
 8901  AAGAGCAGAA ATTCTACACT TTCCTAAAGG TAAGTGAGCT GCCACCTGTG
 8951  CTGGCTGGGG CTGCAGCCCC TCCTGGCTCC AGCCCACAGC GTCAGGGCCC
 9001  ATGCCACCTC CCCTGCTCCT GGGCTCTTGG GGAATTTCTT GGCACCTGAC
 9051  TATTGTTCCA ACTAGAGGGC TCTGCAGACC CTGACTAGGG TCTCATTGGC
 9101  CCATTTTACA GAAAGGCCCA GAAGGACCCA GAGTGAACAT ACTAAGGGTC
 9151  TCACAATCTT CTAGAGCCAC AGCTGGCGCT GGCAGTCTTC TAACTCCCAA
 9201  ACTGGGGCTC TTTTCTCAGG GCCAGGCTAT TCCCCAGGAA GGCCTGGGAA
 9251  GGAAGAGGGT CAGGGGGCCT CAAGCAAGGT TGACACTCCT CTCATCCCTG
 9301  CTCTAGAACT CCTGTCCTCC CACCTCGGAG CTCCTGGGTA CATCTGACCG
 9351  CCTCTTCTGG GAACCCATGA AGGTTCACGA CATCCGCTGG AACTTTGAGA
 9401  AGTTCCTGGT GGGGCCAGAT GGTATACCCA TCATGCGCTG GCACCACCGG
 9451  ACCACGGTCA GCAACGTCAA GATGGACATC CTGTCCTACA TGAGGCGGCA
 9501  GGCAGCCCTG GGGGTCAAGA GGAAGTAACT GAAGGCCGTC TCATCCCATG
 9551  TCCACCATGT AGGGGAGGGA CTTTGTTCAG GAAGAAATCC GTGTCTCCAA
 9601  CCACACTATC TACCCATCAC AGACCCCTTT CCTATCACTC AAGGCCCCAG
 9651  CCTGGCACAA ATGGATGCAT ACAGTTCTGT GTACTGCCAG GCATGTGGGT
 9701  GTGGGTGCAT GTGGGTGTTT ACACACATGC CTACAGGTAT GCGTGATTGT
 9751  GTGTGTGTGC ATGGGTGTAC AGCCACGTGT CTACCTATGT GTCTTTCTGG
 9801  GAATGTGTAC CATCTGTGTG CCTGCAGCTG TGTAGTGCTG GACAGTGACA
 9851  ACCCTTTCTC TCCAGTTCTC CACTCCAATG ATAATAGTTC ACTTACACCT
 9901  AAACCCAAAG GAAAAACCAG CTCTAAGTCC AATTGTTCTG CTCTAACTGA
 9951  TACCTCAACC TTGGGGCCAG CATCTCCCAC TGCCTCCAAA TATTAGTAAC
10001  TATGACTGAC GTCCCCAGAA GTTTCTGGGT CTACCACACT CCCCAACCCC
10051  CCACTCCTAC TTCCTGAAGG GCCCTCCCAA GGCTACATCC CCACCCCACA
10101  GTTCTCCCTG AGAGAGATCA ACCTCCCTGA GATCAACCAA GGCAGATGTG
10151  ACAGCAAGGG CCACGGACCC CATGGCAGGG GTGGCGTCTT CATGAGGGAG
10201  GGGCCCAAAG CCCTTGTGGG CGGACCTCCC CTGAGCCTGT CTGAGGGGCC
10251  AGCCCTTAGT GCATTCAGGC TAAGGCCCCT GGGCAGGGAT GCCACCCCTG
10301  CTCCTTCGGA GGACGTGCCC TCACCCCTCA CTGGTCCACT GGCTTGAGAC
10351  TCACCCCGTC TGCCCAGTAA AAGCCTTTCT GCAGCAGCTG AGCCTACTGT
10401  GTGTGGTGCT TCTTCAATGG TGGCCGCCCC CGCCTGGGTG GGAAGTGAGG
10451  AGGAGAAGGT GGGGCAGGGT AAAGGGGGGA GGATGAGAAA AGAACAAATA
10501  TGACAACAAA AACTTTTTAC AGTGGGTGCA AAGGTAATTG CGGTTTTTGC
10551  CATATGGCAA AATCCAAGGC TACCTCCCCA CCCCACAATT CTCCCTGAGA
10601  TCAGCCAAGG CAGACTGCAA GGGCCATGTA GCCCTATTAG GGGTGGCATC
```

```
10651  TTCATGAGGG AGGCCCCCCT GCCACAAAAA AGGGGCAAAA ATTGCAATTA
10701  CTTTTTCAAC AACCTGATAG TTAGCTGCAG TGGCGCACTC CTTCAGCTAC
10751  TTGGGAGACT GATGTGGGAG GCTCCCTTGA GCCCGGGAGT TTGAGGCTAT
10801  AGTGTGCCGT GACTGAGTCT GTGAAGAGCC ACTGCACTCC AGCCTGGGCA
10851  ACACAGTCAG ACTGTCTCTT AAAAAAAAAA AAAAAAAAGA GAGAAATTAG
10901  ACAATGCTTT GAGTCCCTGC TTTTTGGCTC CTACCTTGGC CCACTCTGCT
10951  TCTCTCACTC AGCATTTGGA GTTTATAAAA CCAGTTCTGA TCTACTCTCA
11001  TTCCCTCCCA CAGTTCTCCA AGTCAGCTGA GGTTAAGATG AGGTGTTCTG
11051  TTTGACGGAT GAGGAAACTG AGGCTCACAG AAGGGCCACG CCTTGCCCCA
11101  GGTCTCCTGA TGAGTGAGGG GCAGGACTGG AATTTAAACC CAAGTCCCCT
11151  GAGTCCTGGC CTAGGCTCCT TCCACTGCCC CGGCTGCCCT ACCCTCAGGG
11201  AGGCCCTGAT ACGTCACCAT TACTCAAGAG TAATGGTGAC CATCTCAGGG
11251  AAAGGAAGAA AAGGGGAACA GAAGGAGGGA CCCAGGAAAG CAGGGGGTTG
11301  ACAGGGGAAC ATTAGCGCAT AAATGAACAT GACTCAGAAT GTTGATCTTC
11351  TTCAACTTGG ATTTATGTCC ATGATTCGTG CAAATAGCTA TCCAGGGATG
11401  GACAGCCACC CTAATCTGGG CTTCTGGCAC CACAGGCCTC CAGCTATGGG
11451  GTCCAGGGTC TGAACCTCAG GGCCTGGCAG CTTCAGGCTG GCGCCCCTCG
11501  GCGGACGTGG CTGGCATGGC CTTCTCCCAT CTGTGATGGC TTCAGCAAGG
11551  CTACTGTGAG TGGTGGTGGA GAGGGCCCCA GAGCCAGAAT ATCCATCATT
11601  CTCTTCTGTT CTGGAGACAA ACCCACACTT CCCACAGCCTC CTCACAGAGG
11651  GGTAGGGGTG TGCGTGGGGC AGGTCCTGCT ACAGAGCTTG AAGCAAAAAT
11701  TAAACACACA CACAAATTGG TCATGGCAAC TAGAGGGCCT GAAACCACTT
11751  CCGGGAGGTT TTGAAGGAAG GGGTCTTGG CTGCCTCCCA CTCTTAGGAT
11801  TGCTGCTCCT GGAGGCTTCT GCAACGGATG GTGGGTCAAA GCCGGATGAG
11851  GCCTCTCTCC ACTCAGCAGC AGGGAAGGAG TTTTTCCCAG TCACTCCCAG
11901  CAGAGTACAA ATGAAAGCCT TCTGGGTGGA GCCTCCCCAG TCCTGTAAAC
11951  AGCTCAGTTC AGGGACTGGT ATACAAGCTG GCCACCCATC TCAGCCTCTC
12001  ATCCAGCTGA GGCTCTGGCC ACACCGTGCA AGTGGCTTCT AGTTTCTTGG
12051  CAATCTGAGA TCAGCTGGCT CTGCAAGATG AAGGTGGAGC CAAATGACAC
12101  AATCTGGTCT CACTGAGGCC CCTCACGGTC ATTTTTGGA GACTCTAAAT
12151  AAACAAAAAT TTTGAGGACT TCATGATTAT GTGGTAGAGC GAGTTTCAAA
12201  GTCTCTTATG GAATGCAGTG CAGGAACAGT GAAAATAACA GCTAGGGTTA
12251  CTGGGTGCTA CCAAGTGCCA GGGCTAAGTA CCTTAAGTAC GCTGGTCATG
12301  TAATCTTCAC CCAGCCCTAT GAAGAAGGCA GGTTATTATC CCATTGTAAA
12351  AGAGGGAACT GGGACACTAA GAGGTTTTAA ATGAC
       (SEQ ID NO: 3)
```

FEATURES:
Start: 2057
Exon: 2057-2139
Intron: 2140-2225
Exon: 2226-2252
Intron: 2253-6737
Exon: 6738-6891
Intron: 6892-8297
Exon: 8298-8415
Intron: 8416-8829
Exon: 8830-8929
Intron: 8930-9306
Exon: 9307-9525
Stop: 9526

Chromosome map:
Chromosome No: 5

FIGURE 3, page 4 of 4

US 6,468,774 B1

ISOLATED HUMAN ENZYME PROTEINS, NUCLEIC ACID MOLECULES ENCODING HUMAN ENZYME PROTEINS, AND USES THEREOF

FIELD OF THE INVENTION

The present invention is in the field of enzyme proteins that are related to the glutathione peroxidase subfamily, recombinant DNA molecules, and protein production. The present invention specifically provides novel peptides and proteins and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the glutathione peroxidase subfamily.

Glutathione peroxidase (EC 1.11.1.9) catalyzes the reduction of hydrogen peroxide, organic hydroperoxide, and lipid peroxides by reduced glutathione and functions in the protection of cells against oxidative damage. This enzyme, found mainly in the cytosol of mammalian cells, is unusual in its content of a selenocysteine residue in its active site that is encoded by a TGA opal codon (Chambers et al., 1986). The glutathione peroxidase found in plasma is immunologically distinct from the erythrocyte and liver cytosolic enzymes. It also has some differences in physical and kinetic properties. Takahashi et al. (1990) isolated cDNA clones coding for plasma GPX. They found that the nucleotide sequence consisted of a 678-bp open reading frame coding for a 226-amino acid polypeptide with a molecular mass of 25,389. The amino acid sequence showed only 44% homology with human cellular GPX. Northern blot analysis showed a single transcript of 2.2 kb in the polyadenylated RNA fractions of human placenta and of a human hepatic cell line, HepG2, but not in those of human liver and endothelial cells. Takahashi et al. (1990) concluded that as the plasma enzyme contains 1 atom of selenium per subunit, the in-frame TGA observed at positions 217–219 could be assigned to selenocysteine.

Chu et al. (1992) found that glutathione peroxidase-3 is expressed in kidney, lung, heart, breast, placenta, and, in the human but not the rodent, in liver as well. By Southern analysis of genomic DNA from human/hamster somatic cell hybrids, Chu (1994) mapped the GPX3 gene to chromosome 5.

The present invention has substantial similarity to human plasma glutathione peroxidase (GSHPx). HSHPx has been shown to be a selenium-containing enzyme immunologically distinct from cellular GSHPx. Nucleotide sequence analysis of the obtained clones revealed that GSHPx consisted of a 678-base pair open reading frame coding for a 226-amino acid polypeptide with a Mr of 25,389. About 50% of the deduced amino acid sequence was confirmed by partial amino acid sequencing of the peptides in a lysine endopeptidase-digest of the purified enzyme. Northern blot analysis revealed a single transcript of 2.2 kilobases in the poly(A)+RNA fractions of human placenta and HepG2 (a human hepatic cell line), but not that of human liver and endothelial cells.

Tujebajeva et al., EMBO Rep 2000 Aug;1(2):158–63; Takahashi et al., J Biochem (Tokyo) August 1990; 108(2):145–8; Chambers et al., EMBO J. 5: 1221–1227, 1986; Chu et al., Cytogenet. Cell Genet. 66: 96–98, 1994; Chu et al., Blood 79: 3233–3238, 1992.

Enzyme proteins, particularly members of the glutathione peroxidase subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the glutathione peroxidase subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the glutathione peroxidase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver.

DESCRIPTION OF THE FIGURE SHEETS

FIG. 1 provides the nucleotide sequence of a cDNA molecule sequence that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the glutathione peroxidase subfamily. Utilizing these sequences, additional genomic sequences were assembled and transcript and/or cDNA sequences were isolated and characterized. Based on this analysis, the present invention provides amino acid sequences of human enzyme peptides and proteins that are related to the glutathione peroxidase subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the glutathione peroxidase subfamily and the expression pattern observed. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known glutathione peroxidase family or subfamily of enzyme proteins.

Specific Embodiments

Peptide Molecules

The present invention provides nucleic acid sequences that encode protein molecules that have been identified as being members of the enzyme family of proteins and are related to the glutathione peroxidase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals.

The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http:H/www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at DJS May 17, 2002 www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol.*

*Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. As indicated by the data presented in FIG. 3, the map position was determined to be on chromosome 5 by ePCR.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. As indicated by the data presented in FIG. 3, the map position was determined to be on chromosome 5 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below. Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver. A large percentage of pharmaceutical agents are being developed that modulate the activity of enzyme proteins, particularly members of the glutathione peroxidase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the glutathione peroxidase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L- configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemicalibiological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, MO) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques.

For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, MRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and nonconservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 5 by ePCR.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length length cDNA and genomic clones encoding the peptide described in FIG. 2 and to isolate cDNA and genomic clones that correspond to variants (alleles, orthologs, etc.) producing the same or related peptides shown in FIG. 2.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 5 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in the brain glioblastoma cell line, ovary adenocarcinoma cell line, panceras epitheloid carcinoma, uterus leiomyosarcoma, lung large cell carcinoma, fetal brain and human whole liver.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. As indicated by the data presented in FIG. 3, the map position was determined to be on chromosome 5 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to core for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/1 6101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in the brain glioblastoma cell line, ovary adenocarcinoma cell line, panceras epitheloid carcinoma, uterus leiomyosarcoma, lung large cell carcinoma and fetal brain detected by a virtual northern blot. In addition, PCR-based tissue screening panels indicate expression in the human whole liver. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/25 1116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., Techniques in Immunocytochemistry, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene 69:301–315* (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943 (1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd*, ed., *Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence(s) can be operably linked to the transgene to direct expression of the enzyme protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a protein comprising the amino acid sequence of SEQ ID NO:2;
   (b) the nucleotide sequence of SEQ ID NO:1;
   (c) the nucleotide sequence of SEQ ID NO:3; and
   (d) a nucleotide sequence that is completely complementary to a nucleotide sequence of (a)–(c).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the polypeptide from the host cell culture.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, virus, and bacteriophage.

8. A vector according to claim 2, wherein said isolated nucleic acid molecule is inserted into said vector in proper orientation and correct reading frame such that the protein of SEQ ID NO: 2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 1666
<212> TYPE: DNA
<213> ORGANISM: Human

<400> SEQUENCE: 1

| | | | | | |
|---|---|---|---|---|---|
| gccagggatc | aggcagcggc | tcaggcgacc | ctgagtgtgc | ccccaccccg | ccatggcccg | 60 |
| gctgctgcag | gcgtcctgcc | tgctttccct | gctcctggcc | ggcttcgtct | cgcagagccg | 120 |
| gggacaagag | aagtcgaagg | ctccccgcca | gatgggcaat | ccccagatgg | actgccatgg | 180 |
| tggcataagt | ggcaccattt | acgagtacgg | agccctcacc | attgatgggg | aggagtacat | 240 |
| cccttcaag | cagtatgctg | gcaaatacgt | cctctttgtc | aacgtggcca | gctactgagg | 300 |
| cctgacgggc | cagtacattg | aactgaatgc | actacaggaa | gagcttgcac | cattcggtct | 360 |
| ggtcattctg | ggctttccct | gcaaccaatt | tggaaaacag | gaaccaggag | agaactcaga | 420 |
| gatccttcct | accctcaagt | atgtccgacc | aggtggaggc | tttgtcccta | atttccagct | 480 |
| cttttgagaaa | ggggatgtca | atggagagaa | agagcagaaa | ttctacactt | tcctaaagaa | 540 |
| ctcctgtcct | cccacctcgg | agctcctggg | tacatctgac | cgcctcttct | gggaacccat | 600 |

-continued

```
gaaggttcac gacatccgct ggaactttga gaagttcctg gtggggccag atggtatacc    660
catcatgcgc tggcaccacc ggaccacggt cagcaacgtc aagatggaca tcctgtccta    720
catgaggcgg caggcagccc tgggggtcaa gaggaagtaa ctgaaggccg tctcatccca    780
tgtccaccat gtaggggagg gactttgttc aggaagaaat ccgtgtctcc aaccacacta    840
tctacccatc acagacccct ttcctatcac tcaaggcccc agcctggcac aaatggatgc    900
atacagttct gtgtactgcc aggcatgtgg gtgtgggtgc atgtgggtgt ttacacacat    960
gcctacaggt atgcgtgatt gtgtgtgtgt gcatgggtgt acagccacgt gtctacctat   1020
gtgtctttct gggaatgtgt accatctgtg tgcctgcagc tgtgtagtgc tggacagtga   1080
caaccctttc tctccagttc tccactccaa tgataatagt tcacttacac ctaaacccaa   1140
aggaaaaacc agctctaggt ccaattgttc tgctctaact gatacctcaa ccttggggcc   1200
agcatctccc actgcctcca aatattagta actatgactg acgtcccag aagtttctgg    1260 gtctaccaca ctcccccaacc ccccactcct acttcctgaa gggccctccc aaggctacat   1320
ccccacccca cagttctccc tgagagagat caacctccct gagatcaacc aaggcagatg   1380
tgacagcaag ggccacggac cccatggcag gggtggcgtc ttcatgaggg aggggcccaa   1440
agcccttgtg ggcggacctc ccctgagcct gtctgagggg ccagcccctta gtgcattcag   1500 gctaaggccc ctgggcaggg atgccacccc tgctccttcg gaggacgtgc cctcacccct   1560
cactggtcca ctggcttgag actcacccccg tctgcccagt aaaagccttt ctgcagcaaa   1620
aaaaaaaaaa aaaaaaaaaa aaaaaaaaaa aaaaaaaaaa aaaaaa                  1666
```

<210> SEQ ID NO 2
<211> LENGTH: 235
<212> TYPE: PRT
<213> ORGANISM: Human

<400> SEQUENCE: 2

```
Met Ala Arg Leu Leu Gln Ala Ser Cys Leu Leu Ser Leu Leu Leu Ala
 1               5                  10                  15

Gly Phe Val Ser Gln Ser Arg Gly Gln Glu Lys Ser Lys Ala Pro Arg
            20                  25                  30

Gln Met Gly Asn Pro Gln Met Asp Cys His Gly Gly Ile Ser Gly Thr
        35                  40                  45

Ile Tyr Glu Tyr Gly Ala Leu Thr Ile Asp Gly Glu Glu Tyr Ile Pro
    50                  55                  60

Phe Lys Gln Tyr Ala Gly Lys Tyr Val Leu Phe Val Asn Val Ala Ser
65                  70                  75                  80

Tyr Cys Gly Leu Thr Gly Gln Tyr Ile Glu Leu Asn Ala Leu Gln Glu
                85                  90                  95

Glu Leu Ala Pro Phe Gly Leu Val Ile Leu Gly Phe Pro Cys Asn Gln
            100                 105                 110

Phe Gly Lys Gln Glu Pro Gly Glu Asn Ser Glu Ile Leu Pro Thr Leu
        115                 120                 125

Lys Tyr Val Arg Pro Gly Gly Phe Val Pro Asn Phe Gln Leu Phe
    130                 135                 140

Glu Lys Gly Asp Val Asn Gly Lys Glu Gln Lys Phe Tyr Thr Phe
145                 150                 155                 160

Leu Lys Asn Ser Cys Pro Pro Thr Ser Glu Leu Leu Gly Thr Ser Asp
                165                 170                 175

Arg Leu Phe Trp Glu Pro Met Lys Val His Asp Ile Arg Trp Asn Phe
            180                 185                 190
```

```
Glu Lys Phe Leu Val Gly Pro Asp Gly Ile Pro Ile Met Arg Trp His
        195                 200                 205

His Arg Thr Thr Val Ser Asn Val Lys Met Asp Ile Leu Ser Tyr Met
        210                 215                 220

Arg Arg Gln Ala Ala Leu Gly Val Lys Arg Lys
225                 230                 235

<210> SEQ ID NO 3
<211> LENGTH: 12385
<212> TYPE: DNA
<213> ORGANISM: Human

<400> SEQUENCE: 3
aacacctttg agagcaggga ctttggcttt tagacaactc tttagcatct ctcatggtgt      60
taacatgttg ctaggtgcct atttttgaggg tcactagatg cctactgata ctaatgaaca    120
atggatttct gacaaactga tgtgcacaca gatgtttata ttttagggta aatacgaacc    180
ttaaaagaca acagaacaac atggagaggg cctgagactg agtctagaga cctggattct    240
ggttccctcc ctgccatcag ttggttatgg gaacttggat aaaattgctcc tcatctctag    300 gcttcaggga aatgaggtgg ttgaataaaa cgtattgagc acttactgtg tgtcagccat    360
tgttcatatg ctcccaggct ttaactcagc taaagacttc cctggcctct gtggttcctt    420
ccacttcaac aggctgtggt ttgaggtggg aagacttcgt agagaatgca aaacttgaga    480
gacatcttcc aaattcccag ggggatgtta ataccttttaa tcatagtaaa ggtatggttt   540
ctcaaggcat tcttggtca gaagaaagtt ccagaaggca cttaatccta ggactcacac    600
taccaaggct acagccaggc caactgcctc acaataacct tagaacatgt ctgaagacag    660 atttttcagct tctgccccta gagattctaa tgcagtgatt ccaaagtggg gtccaggaat    720
ctgtattaaa ggcttcccag ttgactctgg tggtcagaga gatttgagac tgattccatc    780
acattcccca tctgtgaacg ggatcatacc tagacagccc agccctagaa ctgcctggtc    840
tgatcctaag tgttccatgg agattttgtt tttttaatgt aatgaatgat taagtcagca    900
aatactttac atctcttgtg tgctaggccc tgtgccaggt ggtgattatg ggccctattc    960
tcaaaggact cctggtctcc gtctgtcact tactttagaa acaagtcatc tagccagagc   1020
cagaagggca ctggagatca ctaatcaatc ccatcattac atagctgagg aaactgaggc   1080
ccagagagta actgcaacat gttaaagact acacagggag caaatttatt ttctgcttct   1140
aagccaggtg gtttggccac agataggcca agaagaatac gaacagacaa gccttgctgg   1200
gtttcccact cagtttatta ctattagacc attccctttt tccccactca catttctgcg   1260
catttccatg gtcttcatag aatctaagcc taaaaataga gttttccttg agtctttggg   1320
tcttcatttc tgaagactct catgtcacag aaaactttaa ttaaataaat cgttatgctt   1380
ttctcttgct aacctttttc tacaggcatg tcagctgtga tccttatgat ggggaggaaa   1440
ggcaccccac cttctctgtc cctacagtcc taatgcccta cccagaatgg ggttttcaaa    1500
atcccaggac acccactctt tgtttcttaa gcactaaacc tatatatagt aaatgtttct   1560
ggaagtttaa cttcagctct tgctgaaatt ttaaaccctc aatttccaga ggaccatcgc   1620
caggtgtttt taaaacctcg ataggaataa gaaatgcttc ccagaatgga gacttccatc   1680
agttctaggg agctattagc ccccttgccc tggctgtaat ggagaccgct gtgtctgcct   1740
cctttcgcac tttggagcca aaagaggaag ggaccgcctc ccacgtccac agggacctga    1800
cttccacctc tctgcccaga tttgcttatg tcactgtcgc cccgggacgg ggaggtgggg   1860
```

```
agctgagggc aagtcgcgcc cgcccctgaa atcccagccg cctagcgatt ggctgcaagg   1920
gtctcggctt ggccgcggat tggtcacacc cgagggcttg aaaggtggct gggagcgccg   1980
gacacctcag acggacggtg ccagggatc aggcagcggc tcaggcgacc ctgagtgtgc   2040
ccccaccccg ccatggcccg gctgctgcag gcgtcctgcc tgctttccct gctcctggcc   2100
ggcttcgtct cgcagagccg gggacaagag aagtcgaagg tgagtgagcc tccgggccgg   2160
gggccgggag aaaaaaccta gcccctcggt gtccagcgct cagtgcaatg cacccctttt   2220
cccaggctcc ccgccagatg ggcaatcccc aggtgcgaga gacctcctga acccctttg    2280 ccgcccctc cgccgccggg accccgcccc cgaccgtcgt cgtctcgtag ttccatctgt    2340
tggagagccg agacctggtg cttcaggcgg gcagaatgac taagggagga aggtctctct   2400
ccccgagctc gcactttctc cccactgcca cctcgagggt cgccttgcta catctatgtc   2460
acctccgtgc ctgagctgct cccccttcagt agggcctaag agggagggcg tcacagaaaa   2520
aaatgcccag cgtctgggtg ggctgtgcaa gttcccaggg agagagacaa ggagaaagga   2580
gagaggcagc tgggtggtcc tggtcctgaa gaactgctgt gggggctct  tctaccccaa    2640 gaatgataca ggcaggtaga aatggccact tggattcagg gcattggtag aagaggcaga   2700
gatctgtgct agaaagagct ctggagtgac agtgcagaac actcaggacc ctgagtcctt   2760
acctgctcct ggacccccgt ttctccatct gcaggggaga gtttgggggt gggagtgcat   2820
ggggcacaat gaagctgagg gcctcagagg ggatgcttgg agaagctgaa aaatccacaa   2880
gctgttctct gaaatttcct cccctggggc agcctcacta cccaggaccc actgtcctca   2940
ttagcctgag gaaacctggt agttggagaa agctgggggac tgctaattca gaagaagagg   3000
tagaattctc tagagcctca gtctatttcc agcaggtgtg tggcccacac ctggagtggg   3060
gatactgagg ccaggagtgg gatgacccag catgcttatc tcctttgaca gtatgtactg   3120
gggtgggctc tgtagacctc tcctctaccc agggagtggg agtgggtggg aaggaggca    3180 gaagccaggt gtagggatag actcaaagcg agcgatttct gtctccaact tcccaacatg   3240
cataactcac attttgcaa gctctgagct tttgtttcta aaatcctctg ggtcttcact    3300
ttaattaagt tcttatgagt ctaggattcc gtttccaaaa ttctgtccac ttctcaggaa   3360
gcccattgga agcacagggt tccttccatg ttactcaccc cttttcggtc ctcagcctaa   3420
atccgattaa tcagcctctc cttggagtca gtctaaatgg atgtgaagcc acttcgtcca   3480
agtcccctcc tttttatcca tccctgttca taatccccaa ctcagaaggc attttccagg   3540
tcaggaatgg gatcgatttt caacattgag gtttggggtg ggccatagac aggccagcac   3600
cgtggagtca gtcccaacct tcagttttgg aagggtcaaa gaagatacaa ttgggccctg   3660
cctcaagaag gctagtgggg agaacgtgga ctccatgaat aactcatcat agctgtgtct   3720
tctctgccgc actctgggga aggataaatg gactcagaga gaataggatg gggatggtct   3780
agaaaagttt tagggtgagg tgtgatcata tcacatacaa ccagtcagga cttgctggct   3840
aatgaaagcc tgggcatgcc catctctgct cccaagttct tagagttcag atgtcttagc   3900
tctgggttag gacccaacca ctcaccttac ccccaacccc agggtaaaga gatagggtta   3960 tgggcatgt ggagaatgga atggacgaaa ggtgactcag ccccagagag gtgttttcct    4020
cctaccaatt gaaagggaga tgctagggaa gagaccaggt cctcctcttc ttgctgcgtc   4080
acctccccag tccaacttca ggctgcccac gctccttgtc tctacaaaag gactgcagaa   4140
gccggaaaga gtgacaactg ctgacgtgca tgggatccta gtaactgctg gtttctaggt   4200
```

```
gactaaacct ggcagagaga atcatggaac cacaggctga cagagttaaa gggcccttaa    4260
gacagccctg aacctgactc catcttacaa tggaggagct ggagcccag caaggggt      4320 cacatgccat cagagacaca gcaaagccca gcactcaggt ctcctgactc ccagaccact   4380
tctcacagca tcatattgat aggagtgata agacgggaga ggagaaagac acaagaccag   4440
cagccccagc cagccagagt cctggctgag tcccatcatc caactctcaa gccattggaa   4500
ccctcttctc ttgcccggct gtgggaggat tcaggcaccc tcatggcctc tcccttatc    4560 tcctctggcc actgtttcag atgcggtgct ctgggattcc acgtgcccag agaagggaag   4620
ggggctcata gaggactgag ttgcagtgat cagtggtgag cacagccgtg gctctccacc   4680
catgggccac cttctgaccc ccactatccc ttgacatgaa atttcgttcc aagagactcc   4740
aggcctgttt tgctctgcca gcagattccc acaaccgttt gggcagcag catgcttatc    4800 tccctggaca tatgcccaga cagtgtaagt gacttgctca gggccacgca gccagcaaaa   4860
aatagaacct aatgaaatag ggttctcctt gccacacccc caagctgaaa ctgtgcccag   4920
aagctggtcc ttctgtttac aagttcccat tattaggaca acctgtaatc tttttttcct   4980
ccatgtctca gagttcattt ttggatcatg gcagagttaa aaaagtggag aggctataga   5040
catgcctggc tttctggcca ctagatcttt gtggcggtct agggtgtatt tgttgtgccc    5100
cagtttgtct gcattttaag gcggaactgg ccctggctgg gaacgaggag gtccaggagc   5160
agtaggaatg ttgatcttag gtcttgggcc tgcctccagc acccaccaaa agtcaccgga   5220
tgtggaatat tagactcatg taaagcagga agtttgcacc agagccaaga agagagcttg   5280
cagctgccag ggaatggcct ggcggaggaa gcgcagcctc gcccagctca gcagacctgc   5340
ttcatgacag aggcagctct tctgcactct actgggccca cgccctgcca gcatatatca   5400
ctcccttcac ctggtcaggc ccaggtacct tgcctcaaca gcaagttctc cagaattgag   5460
gggaagagag ggagtgaatt tgcttctcta actccagcca cctgtctctg ccctctcctg   5520
gtctataatg ctactttgca ttccatttgt ttattgtctg cccacctctc aaaggatatc   5580
agggccacaa aggaccttaa agaccacctt atacaatggt ttcaaggttt ctcctttccc   5640
atcacgacca gcccacctgc caaattgtgt caatgatgca atgacatcct ttcaagaata   5700
gtctcagaat tttgttgtct gtgtcacggg cagagtaggc tcataggcca catcctacta   5760
gccagcagtg accccaatcc cctctctccc actgatcatg atcctatcaa gccatcatgg   5820
ttgacctggt tgaagagttg gttcagttca aggttctcat tttataaatg aggaaactca   5880
ggtccgaaga aaagaaaggg ccagtccaag accacacagg gagttaatgg cagagggaca   5940
tggagcccag gtctcccagc ccacagtcca ctgcactctg tccctccttg tcctggaggc   6000
tgactgtgag cagcagctgg ggagggagga aggcataagg gtcatcacca gcctgctcag   6060
acccggaaca ttaacacatg caggtactgt tgcttttccc tacctcacca cagcccttc    6120 ccccatgcct ggctctcagt cctgcttccc tatttggtaa caacagcttc atctttcctg   6180
tcctgcagat tgggagcctc tgaatcacca tgtccatact gcctcttcct cctttctgtt   6240 cagttttcc ttcacactgg cctagttcag gttctcatcc tcaattgcct ggattattcc    6300
aacagccacc caaccagtct ccatcagccc gtctaggaac ccagtcatca gctttagggc   6360
agtctccctg agagcccagt aaatgttctg aaattgacat gtgatgtgga agtaattagc   6420
aaaataagtc attctccagg gttccatagc actcacttat taagtgctta atattaataa   6480
gtgcttatta ggtgcttaat attaataagt gcttttaag cacttaatat taagtacccg    6540
aaaagcactt attaagtgct ttcataatca ttatcttaaa caaggaatta ggagacgtca   6600
```

```
gtgctagtcc agttccaatt ctcggtgatt actttgagaa agtcactctc tctgttggga    6660
tctttcattc ttttgaaaac ggagatgtcc aagttccttt ccagctctaa ctgctccttt    6720
tatggcctgt gttccagatg gactgccatg gtggcataag tggcaccatt tacgagtacg    6780
gagccctcac cattgatggg gaggagtaca tccccttcaa gcagtatgct ggcaaatacg    6840
tcctctttgt caacgtggcc agctactgag gcctgacggg ccagtacatt ggtaagagcc    6900
cacccttcct ccctgcttta tttggggctg tatggcatat ttcaatcaca ggagcttttc    6960
tggtgcatgg gggaaagggt gatggcaatc acgagagtcc aagccccttt tctcagctcc    7020
actgtgttcc gtggttttgt gaagatgatt atataagcct gaggtctgat tgcctttgga    7080
catgttctag gagattccta gttatccttc ttcatctctg gcacctcaa caaccctaaa     7140 ggcagaggga tagagattag gtttgtgctt agagctccct ttggctggag catgagatgg    7200
taactgaagc tccatcttgc tgagaatatc tcattttccc tcagcccat ctgctttggt     7260 gcttctcttg gcagctctct ggaaagcagg caattgcctc gaggcccag agtgtatgcg      7320 tggtgtagcg ggatgaagga gcaggctaca cttctaatgc ccattctaaa ataaactttg    7380
aagatgatct agtttagcct tcccctcttc tcaatctaca catgggaaac caagactcag    7440
agcgaagata caacttaaac aggtcacaa agctattagc ggtggaatgg ggcatttggc     7500
gcaggtttca tgatctcctg atatgcttac tcctttctcc ctagctgggg tagaatacag    7560
aggctagggg aacaggcaac caaggcaag cgacagcacc caggggaaaa cgctttgggg     7620
ctgagcagtc tactggcagg gggtcaggga ggcaagggca atttgaccct ccatgctctg    7680
cctggcaatc acaggcgaat tcccggaagt gaaaggacgg cggtcacgtg gcccagtggc    7740
tgtgagtgct ttttctggga tgcttctctc tagccttgga acagagcaga gtgcgtttgg    7800
gcaagagatg ggctgggtgc tgctgcaaaa gagaccaggg gacactgagg aaactgggga    7860
gctgggccag ggcctcatct gtgttcctga tttgcaaag attatgggag ggttgtaacc     7920
tcaccccaaa gaagttctct gccttgtatc cagggatgga tagttcttgc tccagaaaac    7980
tcaatcctga gggttctgaa tgagtgctct agctggccca ggtggagggc cttggcaatg    8040
ggcaggtgac tgacagctga cttgaggaag ggtattattc ttgtcctcca aacctccaat    8100
ccatccagat tagagtcaag aggataggac ctgagtccca gcattgctgt gaactcactg    8160
gtgatcctgc gcaagtccct cccttctctcg ggcctcagta gttccagcgg cacagcgggt   8220
gagccggggg agtggtgtgg atgagacagg gctcctcgcc aggatactcc cacatctgct    8280
ctttctcttt ggcccagaac tgaatgcact acaggaagag cttgcaccat tcggtctggt    8340
cattctgggc tttccctgca accaatttgg aaaacaggaa ccaggagaga actcagagat    8400
ccttcctacc ctcaagtgag tactcactca gcatcctgag aaagctcctc tcacatggcc    8460
cacatcttgt tatcaacccc aaatcatggt ggacatttat cggccaccaa gaactactct    8520
cctcttctag gatccccagt ggaatgaggg aagggaaggg acaagagagg gagaaggaca    8580
gggacaactg gttgtgatgt gcatccgcag ggagcaccaa ggttgaggga cactgaaaag    8640
ggaccaggct agaaaggaag accgtggact cacattatgc ctatgcccac tgcacattca    8700
ctggctcctg ctgcccactg cagaataaat ccagactccc aacaccctct cccctgttct    8760
gtcccttcct ctcatttctg agccctgtgc ccacctcctt gggacccacc taagaacatt    8820
tctcaacagg tatgtccgac caggtggagg ctttgtccct aatttccagc tctttgagaa    8880
aggggatgtc aatggagaga aagagcagaa attctacact ttcctaaagg taagtgagct    8940
```

-continued

| | |
|---|---|
| gccacctgtg ctggctgggg ctgcagcccc tcctggctcc agcccacagc gtcagggccc | 9000 |
| atgccacctc ccctgctcct gggctcttgg ggaatttctt ggcacctgac tattgttcca | 9060 |
| actagagggc tctgcagacc ctgactaggg tctcattggc ccattttaca gaaaggccca | 9120 |
| gaaggaccca gagtgaacat actaagggtc tcacaatctt ctagagccac agctggcgct | 9180 |
| ggcagtcttc taactcccaa actggggctc ttttctcagg gccaggctat tccccaggaa | 9240 |
| ggcctgggaa ggaagagggt cagggggcct caagcaaggt tgacactcct ctcatccctg | 9300 |
| ctctagaact cctgtcctcc cacctcggag ctcctgggta catctgaccg cctcttctgg | 9360 |
| gaacccatga aggttcacga catccgctgg aactttgaga agttcctggt ggggccagat | 9420 |
| ggtatacccca tcatgcgctg gcaccaccgg accacggtca gcaacgtcaa gatggacatc | 9480 |
| ctgtcctaca tgaggcggca ggcagccctg ggggtcaaga ggaagtaact gaaggccgtc | 9540 |
| tcatcccatg tccaccatgt agggaggga ctttgttcag gaagaaatcc gtgtctccaa | 9600 |
| ccacactatc tacccatcac agaccccttt cctatcactc aaggccccag cctggcacaa | 9660 |
| atggatgcat acagttctgt gtactgccag gcatgtgggt gtgggtgcat gtgggtgttt | 9720 |
| acacacatgc ctacaggtat gcgtgattgt gtgtgtgtgc atgggtgtac agccacgtgt | 9780 |
| ctacctatgt gtctttctgg gaatgtgtac catctgtgtg cctgcagctg tgtagtgctg | 9840 |
| gacagtgaca acccttctc tccagttctc cactccaatg ataatagttc acttacacct | 9900 |
| aaacccaaag gaaaaccag ctctaggtcc aattgttctg ctctaactga tacctcaacc | 9960 |
| ttggggccag catctcccac tgcctccaaa tattagtaac tatgactgac gtccccagaa | 10020 |
| gtttctgggt ctaccacact ccccaacccc ccactcctac ttcctgaagg gccctcccaa | 10080 |
| ggctacatcc ccaccccaca gttctccctg agagagatca acctccctga gatcaaccaa | 10140 |
| ggcagatgtg acagcaaggg ccacggaccc catggcaggg gtggcgtctt catgagggag | 10200 |
| gggcccaaag cccttgtggg cggacctccc ctgagcctgt ctgaggggcc agcccttagt | 10260 |
| gcattcaggc taaggcccct gggcagggat gccaccctg ctccttcgga ggacgtgccc | 10320 |
| tcacccctca ctggtccact ggcttgagac tcaccccgtc tgcccagtaa aagcttttct | 10380 |
| gcagcagctg agcctactgt gtgtggtgct tcttcaatgg tggccgcccc cgcctgggtg | 10440 |
| ggaagtgagg aggagaaggt ggggcagggt aaagggggga ggatgagaaa agaacaaata | 10500 |
| tgacaacaaa aactttttac agtgggtgca aaggtaattg cggttttgc catatggcaa | 10560 |
| aatccaaggc tacctcccca ccccacaatt ctccctgaga tcagccaagg cagactgcaa | 10620 |
| gggccatgta gccctattag gggtggcatc ttcatgaggg aggcccccct gccacaaaaa | 10680 |
| agggcaaaa attgcaatta cttttttcaac aacctgatag ttagctgcag tggcgcactc | 10740 |
| cttcagctac ttgggagact gatgtgggag gctcccttga gcccgggagt ttgaggctat | 10800 |
| agtgtgccgt gactgagtct gtgaagagcc actgcactcc agcctgggca acacagtcag | 10860 |
| actgtctctt aaaaaaaaaa aaaaaaaga gagaaattag acaatgcttt gagtccctgc | 10920 |
| tttttggctc ctaccttggc ccactctgct tctctcactc agcatttgga gtttataaaa | 10980 |
| ccagttctga tctactctca ttccctccca cagttctcca agtcagctga ggttaagatg | 11040 |
| aggtgttctg tttgacggat gaggaaactg aggctcacag aagggccacg ccttgcccca | 11100 |
| ggtctcctga tgagtgaggg gcaggactgg aatttaaacc caagtcccct gagtcctggc | 11160 |
| ctaggctcct tccactgccc cggctgccct accctcaggg aggccctgat acgtcaccat | 11220 |
| tactcaagag taatggtgac catctcaggg aaaggaagaa aaggggaaca gaaggaggga | 11280 |
| cccaggaaag caggggttg acaggggaac attagcgcat aaatgaacat gagtcagaat | 11340 |

```
gttgatcttc ttcaacttgg atttatgtcc atgattcgtg caaatagcta tccagggatg    11400
gacagccacc ctaatctggg cttctggcac cacaggcctc cagctatggg gtccagggtc    11460
tgaacctcag ggcctggcag cttcaggctg gcgcccctcg gcggacgtgg ctggcatggc    11520
cttctcccat ctgtgatggc ttcagcaagg ctactgtgag tggtggtgga gagggcccca    11580
gagccagaat atccatcatt ctcttctgtt ctggagacaa acccacactt cccacagctc    11640
ctcacagagg ggtaggggtg tgcgtggggc aggtcctgct acagagcttg aagcaaaaat    11700
taaacacaca cacaaattgg tcatggcaac tagagggcct gaaaccactt ccgggaggtt    11760
ttgaaggaag ggggtcttgg ctgcctccca ctcttaggat tgctgctcct ggaggcttct    11820
gcaacggatg gtgggtcaaa gccggatgag gcctctctcc actcagcagc agggaaggag    11880
tttttcccag tcactcccag cagagtacaa atgaaagcct tctgggtgga gcctccccag    11940
tcctgtaaac agctcagttc agggactggt atacaagctg gccacccatc tcagcctctc    12000
atccagctga ggctctggcc acaccgtgca agtggcttct agtttcttgg caatctgaga    12060
tcagctggct ctgcaagatg aaggtggagc caaatgacac aatctggtct cactgaggcc    12120
cctcacggtc attttttgga gactctaaat aaacaaaaat tttgaggact tcatgattat    12180
gtggtagagc gagtttcaaa gtctcttatg gaatgcagtg caggaacagt gaaaataaca    12240
gctagggtta ctgggtgcta ccaagtgcca gggctaagta ccttaagtac gctggtcatg    12300
taatcttcac ccagccctat gaagaaggca ggttattatc ccattgtaaa agagggaact    12360
gggacactaa gaggttttaa atgac                                          12385
```

<210> SEQ ID NO 4
<211> LENGTH: 226
<212> TYPE: PRT
<213> ORGANISM: Human
<220> FEATURE:
<221> NAME/KEY: VARIANT
<222> LOCATION: (1)...(226)
<223> OTHER INFORMATION: Xaa = Any Amino Acid

<400> SEQUENCE: 4

Met Ala Arg Leu Leu Gln Ala Ser Cys Leu Leu Ser Leu Leu Leu Ala
1               5                   10                  15

Gly Phe Val Ser Gln Ser Arg Gly Gln Glu Lys Ser Lys Met Asp Cys
            20                  25                  30

His Gly Gly Ile Ser Gly Thr Ile Tyr Glu Tyr Gly Ala Leu Thr Ile
        35                  40                  45

Asp Gly Glu Glu Tyr Ile Pro Phe Lys Gln Tyr Ala Gly Lys Tyr Val
    50                  55                  60

Leu Phe Val Asn Val Ala Ser Tyr Xaa Gly Leu Thr Gly Gln Tyr Ile
65                  70                  75                  80

Glu Leu Asn Ala Leu Gln Glu Glu Leu Ala Pro Phe Gly Leu Val Ile
                85                  90                  95

Leu Gly Phe Pro Cys Asn Gln Phe Gly Lys Gln Glu Pro Gly Glu Asn
            100                 105                 110

Ser Glu Ile Leu Pro Thr Leu Lys Tyr Val Arg Pro Gly Gly Gly Phe
        115                 120                 125

Val Pro Asn Phe Gln Leu Phe Glu Lys Gly Asp Val Asn Gly Glu Lys
    130                 135                 140

Glu Gln Lys Phe Tyr Thr Phe Leu Lys Asn Ser Cys Pro Pro Thr Ser
145                 150                 155                 160

-continued

```
Glu Leu Leu Gly Thr Ser Asp Arg Leu Phe Trp Glu Pro Met Lys Val
                165                 170                 175

His Asp Ile Arg Trp Asn Phe Glu Lys Phe Leu Val Gly Pro Asp Gly
            180                 185                 190

Ile Pro Ile Met Arg Trp His His Arg Thr Thr Val Ser Asn Val Lys
        195                 200                 205

Met Asp Ile Leu Ser Tyr Met Arg Arg Gln Ala Ala Leu Gly Val Lys
    210                 215                 220

Arg Lys
225
```